United States Patent
Tanaka et al.

(10) Patent No.: US 11,547,769 B2
(45) Date of Patent: Jan. 10, 2023

(54) LIGHT SOURCE MODULE DEVICE AND FLUID STERILIZING DEVICE

(71) Applicant: Stanley Electric Co., Ltd., Tokyo (JP)

(72) Inventors: Hideaki Tanaka, Tokyo (JP); Hiroyuki Kato, Tokyo (JP); Kazuhisa Shinno, Tokyo (JP)

(73) Assignee: STANLEY ELECTRIC CO., LTD., Tokyo (JP)

( * ) Notice: Subject to any disclaimer, the term of this patent is extended or adjusted under 35 U.S.C. 154(b) by 363 days.

(21) Appl. No.: 16/700,725

(22) Filed: Dec. 2, 2019

(65) Prior Publication Data
US 2020/0171184 A1 Jun. 4, 2020

(30) Foreign Application Priority Data
Dec. 4, 2018 (JP) .............................. JP2018-227038

(51) Int. Cl.
*A61L 2/10* (2006.01)
*A61L 9/20* (2006.01)
*C02F 1/32* (2006.01)

(52) U.S. Cl.
CPC ........ *A61L 2/10* (2013.01); *A61L 9/20* (2013.01); *C02F 1/325* (2013.01); *C02F 2201/3222* (2013.01); *C02F 2201/3228* (2013.01)

(58) Field of Classification Search
CPC .......... A61L 2/10; A61L 9/20; A61L 2202/11; A61L 2/26; C02F 1/325; C02F 2201/3222; C02F 2201/3228; C02F 2201/3227; C02F 2303/04
See application file for complete search history.

(56) References Cited

U.S. PATENT DOCUMENTS

| | | | |
|---|---|---|---|
| 9,540,252 B1 * | 1/2017 | Collins | ................ C02F 1/008 |
| 10,105,460 B1 * | 10/2018 | Collins | .................... A61L 2/10 |
| 10,376,608 B1 * | 8/2019 | Collins | ................. A61L 9/205 |
| 2014/0084182 A1 * | 3/2014 | Kim | ..................... H01L 33/642 |
| | | | 250/492.1 |

(Continued)

FOREIGN PATENT DOCUMENTS

| | | |
|---|---|---|
| CN | 107922214 A | 4/2018 |
| CN | 108136060 A | 6/2018 |

(Continued)

OTHER PUBLICATIONS

Chinese Office Action for the related Chinese Patent Application No. 201911219052.7 dated Sep. 22, 2022.

(Continued)

*Primary Examiner* — Regina M Yoo
(74) *Attorney, Agent, or Firm* — Kenealy Vaidya LLP

(57) ABSTRACT

To provide a light source module device capable of controlling the light distribution of ultraviolet light with a small and simple structure. A light source module device 7 includes a substrate 4, a light source 3 mounted on the substrate 4 and emitting ultraviolet light, a reflector 8 mounted on the substrate 4 so as to surround the light source 3 and reflecting the ultraviolet light by its inner surface to guide the ultraviolet light toward an irradiation target, and a cap-like optical member 9 mounted so as to cover the outer circumference of the reflector 8 and condensing or diffusing the ultraviolet light.

4 Claims, 7 Drawing Sheets

(56) References Cited

U.S. PATENT DOCUMENTS

| | | | | |
|---|---|---|---|---|
| 2016/0083272 A1* | 3/2016 | Rajagopalan | ........... | C02F 1/325 |
| | | | | 250/435 |
| 2017/0290933 A1* | 10/2017 | Collins | ..................... | A61L 9/20 |
| 2019/0142981 A1* | 5/2019 | Kim | ........................ | G01B 5/24 |
| | | | | 250/455.11 |
| 2020/0171184 A1* | 6/2020 | Tanaka | ...................... | A61L 2/10 |
| 2020/0339438 A1* | 10/2020 | Lautzenheiser | ........ | B01D 29/96 |
| 2021/0393817 A1* | 12/2021 | Jeong | ..................... | H01L 33/56 |

FOREIGN PATENT DOCUMENTS

| | | |
|---|---|---|
| JP | H10-233532 A | 9/1998 |
| JP | 2011-016074 A | 1/2011 |
| JP | 2017-64610 A | 4/2017 |
| JP | 2017-104230 A | 6/2017 |
| JP | 2018-064771 A | 4/2018 |
| KR | 2018-0115978 A | 10/2018 |
| WO | 2018/047629 A1 | 6/2019 |

OTHER PUBLICATIONS

Japanese Office Action for the related Japanese Patent Application No. 2018-227038 dated Sep. 27, 2022.

\* cited by examiner

LIGHT SOURCE MODULE DEVICE AND FLUID STERILIZING DEVICE

BACKGROUND OF THE INVENTION

1. Field of the Invention

The present invention relates to a light source module device for sterilizing fluid flowing in a channel with ultraviolet light, and a fluid sterilizing device including the light source module device.

2. Description of the Related Art

In recent years, the sterilizing effect of ultraviolet light (wavelengths of 240 to 380 nm) is utilized for germicidal lamps of food storages or medical equipment. In addition, a device that emits ultraviolet light from an ultraviolet LED to fluid flowing in a channel to sterilize the fluid so that the sterilized fluid is used as cleaning water is well known.

For example, Patent Document 1 mentioned below discloses an irradiation device including a straight pipe, a connection pipe, and a light source. The light source is disposed on an end portion of the straight pipe and emits ultraviolet light toward the inside of the straight pipe to sterilize fluid, such as water, flowing in the straight pipe.

The light source includes a light emitter, a substrate, an adjusting mechanism. The adjusting mechanism includes a first lens, a second lens, and a third lens. With the above, the adjustment mechanism adjusts the light distribution angle of the ultraviolet light emitted from the light emitting device such that the light distribution angle D of the ultraviolet light emitted from the adjustment mechanism is equal to 30 degrees or smaller. This enables transmission of very intensive ultraviolet light along the longitudinal direction of the straight pipe.

PRIOR ART DOCUMENT

[Patent Document]
Patent Document 1: Japanese Patent Laid-Open Publication No. 2017-064610

SUMMARY OF THE INVENTION

However, the irradiation device disclosed in Patent Document 1, whose adjustment mechanism includes three lenses, suffers from a problem in that an interval between the respective lenses and adjustment of the optical axes are necessary. Further, size reduction of the adjustment mechanism is difficult to be achieved, which results in a large device as a whole.

The present invention has been conceived in view of the above, and aims to provide a fluid sterilizing device capable of sterilization with ultraviolet light with a small and simple structure, and a light source module device included in the fluid sterilizing device.

A light source module device according to a first aspect of the present invention includes: a substrate; a light emitting device mounted on the substrate, the light emitting device being for emitting ultraviolet light; a reflector disposed on the substrate so as to surround the light emitting device, the reflector being for reflecting the ultraviolet light on the inner surface thereof to guide the ultraviolet light toward an irradiation target; and an optical member having a cap-like shape and mounted so as to cover the outer circumference of the reflector, the optical member being for transmitting, condensing, or diffusing the ultraviolet light.

According to the present invention, the ultraviolet light emitted from the light emitting device mounted on the substrate is reflected on the inner surface of the reflector to be led toward the irradiation target. As the ultraviolet light is transmitted, condensed, or diffused by the cap-like optical member covering the reflector, it is possible to control the light distribution of the ultraviolet light with a small and simple structure.

In the light source module device according to the first aspect of the present invention, preferably, a portion of the optical member through which the ultraviolet light passes may be formed convex, concave, or planar relative to the open end surface of the reflector.

According to the present invention, a portion of the optical member through which the ultraviolet light passes is formed either convex, concave, or planar relative to the open end of the reflector. With the above, the ultraviolet light is refracted when passing through the optical member. This allows use of an optical member having a suitable shape depending on the dimension or shape of a vessel where the irradiation target is stored.

A fluid sterilizing device according to a second aspect of the present invention includes: the light source module device according to the first aspect; and an enclosure including a channel where fluid to be sterilized flows in the axial direction, at least one inlet through which the fluid flows in, and at least one outlet through which the fluid flows out, wherein the inlet is formed on one end portion of the enclosure in the axial direction, and the light source module device is mounted on an end portion of the enclosure via a sealing member, the end portion being opposite from the inlet.

According to the present invention, the fluid flowing in the channel is irradiated with the ultraviolet light emitted from the light emitting device of the light source module device to be thereby sterilized. In this enclosure, the fluid flows in through the inlet formed on one end portion of the enclosure in the axial direction, and flows out through the outlet.

The light source module device is disposed on an end portion of the enclosure opposite from the inlet. This enables long lasting irradiation of the fluid in the channel with ultraviolet light. In addition, as the light source module device and the enclosure are mounted via a sealing member, the fluid can be prevented from leaking into the light source module device.

A fluid sterilizing device according to a third aspect of the present invention includes the light source module device according to the first aspect; and an enclosure including a channel where fluid to be sterilized flows in the axial direction, at least one inlet through which the fluid flows in, and at least one outlet through which the fluid flows out, wherein the inlet and the outlet are formed on the outer circumference of the enclosure, and the light source module device is mounted on the both end portions of the enclosure in the axial direction via respective sealing members.

According to the present invention, the fluid flowing in the channel is irradiated with the ultraviolet light emitted from the light emitting device of the light source module device to be thereby sterilized. In this enclosure, the fluid flows into the enclosure via the inlet formed on the outer circumference of the enclosure and flows out through the outlet similarly formed on the outer circumference.

Since two light source module devices are provided each on each end portion of the enclosure in the axial direction, it is possible to increase the efficiency in irradiation of the fluid in the channel with the ultraviolet light. In addition, since the light source module device and the enclosure are mounted via respective sealing members, the fluid can be prevented from flowing into the light source module device.

In the fluid sterilizing device according to the second or third aspect of the present invention, preferably, the sealing member seals between the optical member of the light source module device and the end portion of the enclosure.

With this structure, the sealing member is disposed for sealing between the optical member of the light source module device and the end portion of the enclosure. Although sealing members can be deteriorated due to ultraviolet light, depending on the material of the sealing members, as the sealing member according to the present invention is disposed in a position where the ultraviolet light rarely passes, the sealing member can be saved from deterioration.

A light source module device according to a fourth aspect of the present invention includes: a substrate; a light emitting device mounted on the substrate, the light emitting device being for emitting ultraviolet light; a reflector disposed on the substrate so as to surround the light emitting device, the reflector being for reflecting the ultraviolet light on the inner surface thereof to guide the ultraviolet light toward an irradiation target; and an optical lens mounted on an open end portion of the reflector to seal the reflector, the optical lens being for condensing or diffusing the ultraviolet light.

According to the present invention, the ultraviolet light emitted from the light emitting device mounted on the substrate is reflected on the inner surface of the reflector to be led toward the irradiation target. In addition, as the ultraviolet light is condensed or diffused through the optical lens attached to the open end portion of the reflector through welding, for example, this device enables control of the light distribution of the ultraviolet light with a small and simple structure.

A fluid sterilizing device according to a fifth aspect of the present invention includes: the light source module device according to the sixth aspect; and an enclosure including a channel where fluid to be sterilized flows in the axial direction, at least one inlet through which the fluid flows in, and at least one outlet through which the fluid flows out, wherein the inlet is formed on one end portion of the enclosure in the axial direction, and the light source module device is mounted on an end portion of the enclosure via a sealing member, the end portion being opposite from the inlet.

According to the present invention, the light source module device is disposed on the end portion of the enclosure opposite from the inlet. This allows long lasting irradiation of the fluid in the channel with ultraviolet light. In addition, since the light source module device and the enclosure are mounted via a sealing member, the fluid can be prevented from leaking into the light source module device.

In the fluid sterilizing device according to the fifth aspect of the present invention, preferably, the sealing member seals between the reflector of the light source module device and the end portion of the enclosure According to this structure, the sealing member is disposed, thereby sealing, between the optical member of the light source module device and the enclosure. Since the sealing member is disposed outside the reflector, where no ultralight light passes, the sealing member is not irradiated with ultraviolet light and thus can be saved from deterioration.

A light source module device according to a sixth aspect of the present invention includes: a substrate; a light emitting device mounted on the substrate, the light emitting device being for emitting ultraviolet light; a frame abutting on the light emitting surface of the light emitting device, the frame being for supporting the substrate; and an optical member having a cap-like shape, the optical member being supported on the inner circumferential surface of the frame, the optical member being for transmitting, condensing, or diffusing the ultraviolet light, wherein a portion of the optical member through which the ultraviolet light passes is formed convex, concave, or planar relative to the open end surface of the frame.

According to the present invention, since the ultraviolet light emitted from the light emitting device mounted on the substrate is condensed or diffused by the optical member, the present device can control the light distribution of the ultraviolet light with a small and simple structure.

DESCRIPTION OF THE PREFERRED EMBODIMENTS

Embodiments of a fluid sterilizing device according to the present invention will now be described.

First Embodiment

Figure 1:
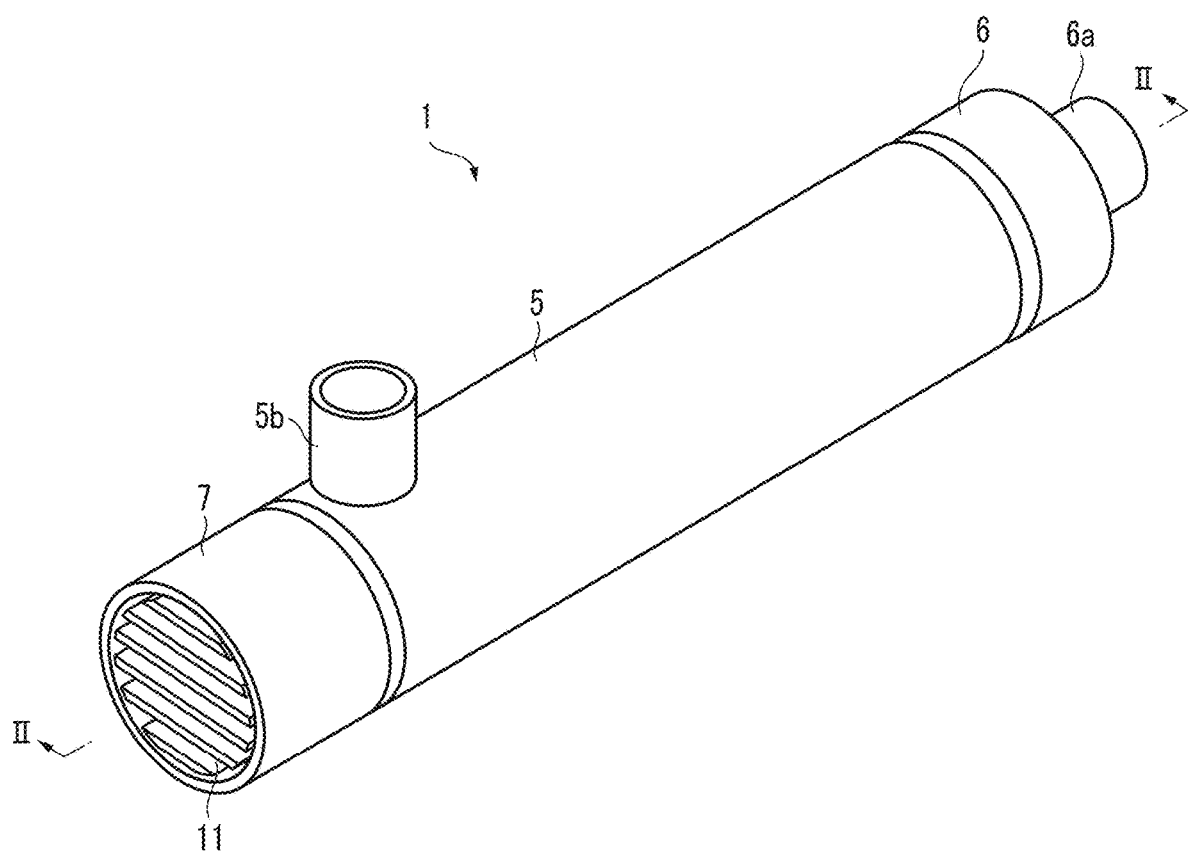
FIG. 1 is a perspective view of an entire fluid sterilizing device according to the present invention (a first embodiment)

FIG. 1 is a perspective view of an entire fluid sterilizing device according to a first embodiment of the present invention. The fluid sterilizing device 1 is a device that irradiates fluid flowing in a channel with ultraviolet light to thereby sterilize the fluid. The fluid sterilizing device 1 is used for water purifiers or industrial circulation devices.

The fluid sterilizing device 1 has a channel, and includes a barrel body 5 (corresponding to an "enclosure" according to the present invention) constituting a sterilizing unit that sterilizes fluid, an inflow device 6 having an inlet for fluid, and a light source module device 7 including a light emitting diode (LED) as a light source.

The barrel body 5 is shaped like a straight pipe whose diameter is 30 mm (the inner diameter of 28 mm) and the length of which channel (the sterilizing unit) is 100 mm Fluid that is a target of sterilization flows in the longitudinal axial direction of the barrel body 5. The barrel body 5 is made of stainless here, though the material of the barrel body 5 differs depending on the purpose. The fluid flows into the barrel body 5 through an inlet 6a (the inner diameter of 13.4 mm) of the inflow device 6, the inlet 6a being formed on one end portion of the barrel body 5 in the axial direction, and flows out through an outlet 5b (the inner diameter of 8.8 mm) formed on the outer circumference of the barrel body 5. In the above, the amount of fluid is 0.5 to 2 (L/min).

The barrel body 5 has a light source module device 7 on its other end portion in the axial direction (on the end portion opposite from the inflow device 6). In the light source module device 7, of which details are to be described later, a light source, a substrate, a reflector, and a quartz cap, for example, are held. On the side of the rear surface of the substrate (the side free from the light emitting surface of the light source), a metal heat sink 11 is provided so that heat generated from the substrate can be discharged.

Figure 2A:
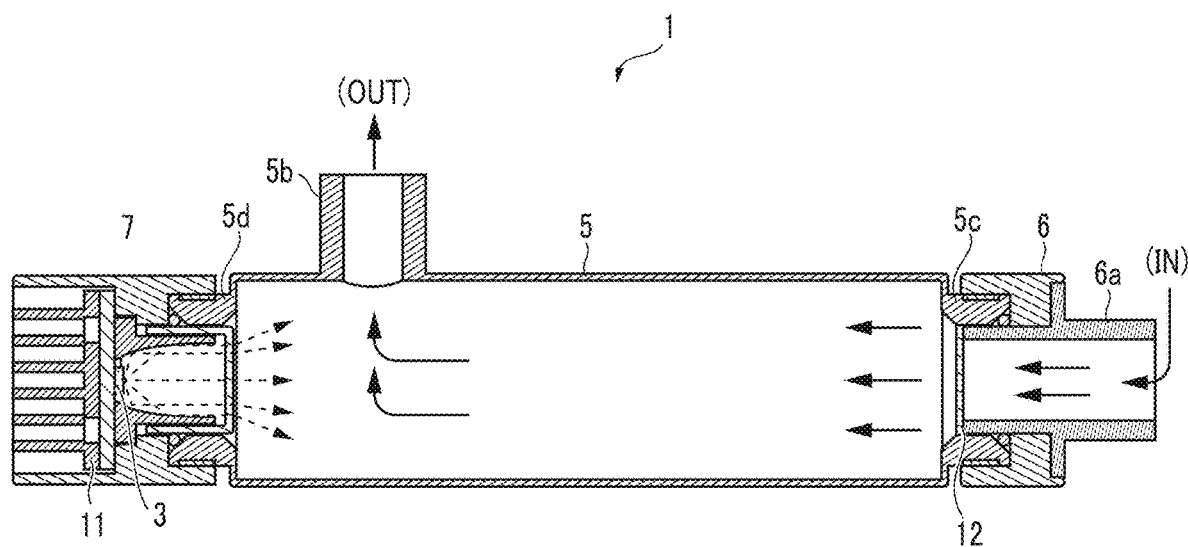
FIG. 2A is a cross sectional view of the fluid sterilizing device in FIG. 1 along the line II-II.

FIG. 2A is a cross sectional view of the fluid sterilizing device 1 in FIG. 1 along the line II-II.

The barrel body 5 has a connection port 5c on its one end in the axial direction (on the right side of the drawing), and a male screw is formed on the connection port 5c. As a female screw is formed on the inner wall of the end portion of the inflow device 6 (made of aluminum) opposite from the inlet 6a, the inflow device 6 can be screwed into the connection port 5c. The fluid having flowed in through the inlet 6a passes through a rectifier 12 provided on an end portion of the inflow device 6 opposite from the inlet 6a to reach the channel of the barrel body 5.

The rectifier 12 is a panel made of metal or fluorine resin and has two or more holes penetrating therethrough in the axial direction of the barrel body 5. As the fluid passes through the rectifier 12, the flow rate of the fluid is averaged when the fluid flows into the channel of the barrel body 5. This enables uniform irradiation of the fluid with ultraviolet light, which increases sterilizing performance.

In addition, the barrel body 5 has a connection port 5d as well formed on the other end portion (on the left side in the drawing) of the barrel body 5 in the axial direction, and a male screw is formed on the connection port 5d. As a female screw is formed on the inner wall of the end portion of the light source module device 7 on the side where the ultraviolet light is emitted, the light source module device 7 can be screwed into the connection port 5d.

The fluid having flowed in through the inlet 6a and reached the channel of the barrel body 5 proceeds toward the outlet 5b of the barrel body 5, and flows out of the barrel body 5. In the above, the fluid in the channel is exposed to the ultraviolet light emitted from a light source 3 of the light source module device 7 and thereby sterilized.

Figure 2B:
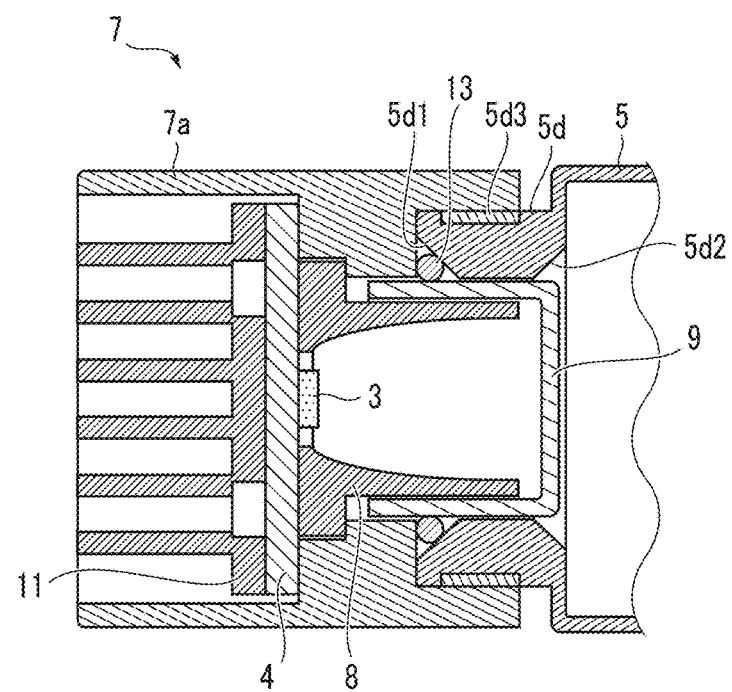
FIG. 2B is an enlarged view of the light source module device in FIG. 2.

FIG. 2B is an enlarged view of the light source module device 7.

As illustrated, the ultraviolet light emitted from the light source 3 has wavelengths that have sterilizing effect or decompose chemical materials, which are wavelengths in the range of 240 to 380 nm, for example. The light source 3 is an ultraviolet LED (corresponding to a "light emitting device" according to the present invention). A single light source 3 is mounted on the side of the front surface of a substrate 4. Alternatively, two or more ultraviolet LEDs can be disposed side by side to be used as a light source.

The substrate 4 is desirably made of metal, such as copper or aluminum, which is superior in heat discharge characteristics. The light source 3 is fed with power via the substrate 4. The substrate 4 abuts on the frame 7a of the light source module device 7 on the side of the front surface of the substrate 4 (the side closer to the light emitting surface of the light source 3), and is securely screwed.

On the side of the rear surface of the substrate 4 (the side opposite from the light emitting surface of the light source 3), the heat sink 11 for discharging heat is provided. This enables efficient discharge of heat generated from the light source 3. In addition, the frame 7a is made of metal, such as aluminum, which is superior in heat conductivity to the barrel body 5, so that heat from the light source 3 is transmitted to the barrel body 5 to be discharged via the fluid as well.

On the side of the front surface of the substrate 4 (inside the frame 7a), a reflector 8 is disposed so as to surround the light source 3. The reflector 8 is a spheroidal or paraboloidal reflection mirror. The ultraviolet light from the light source 3 is reflected on the inner surface of the reflector 8 to proceed toward the channel of the barrel body 5 (refer to FIG. 2A).

The ultraviolet light, reflected on the inner surface of the reflector 8, passes through a cap-like quartz cap 9 (corresponding to an "optical member" according to the present invention), which is mounted so as to cover the reflector 8. The quartz cap 9 is a member made of quartz glass, whose flexibility is larger than that of air, so as to have a substantially uniform thickness. The top end portion of the quartz cap 9, through which the ultraviolet light passes, is formed planar relative to the open end surface of the reflector 8. With the above, the ultraviolet light is refracted and thereby diffused when passing through the quartz cap 9, which enables efficient irradiation of the fluid in the channel with ultraviolet light.

When using a fluid sterilizing device according to the prevent invention, the side of the front surface of the quartz cap 9 is filled with fluid whose flexibility is larger than that of air. The top end portion of the quartz cap 9 may be convex, concave, or of any other shape relative to the open end surface of the reflector 8, as to be described later in detail.

As illustrated, there is a gap between the quartz cap 9 and the connection port 5d of the barrel body 5, and an O-ring 13 (corresponding to a "sealing member" according to the present invention) is disposed in the gap. As a triangular groove 5d1 for the O-ring 13 is formed near the tip end of the connection port 5d, the light source module device 7 can be prevented with sealing from invasion of the fluid thereinto. A triangular groove 5d2 illustrated is a groove that is formed so as to make it easier for the ultraviolet light to pass. A connection portion 5d3 is where the male screw is formed.

Note that the O-ring 13 can deteriorate due to exposure to ultraviolet light even though the O-ring 13 is made of fluorine-based material. The O-ring 13, however, is positioned outside the quartz cap 9 and outside the reflector 8, and thus rarely exposed to the ultraviolet light. This can save the O-ring 13 from deterioration.

As described above, as the light source module device 7 is smaller in dimension compared with a conventional mechanism that adjusts light distribution using stacked lenses, the fluid sterilizing device 1, or the whole device, can be made smaller in dimension.

In the following, modifications of the quartz cap will be described referring to FIG. 3A, FIG. 3B, FIG. 4A to FIG. 4C. Note that the same structure as that in the above-described embodiment is given the same reference numeral and its description is omitted.

Figure 3A:
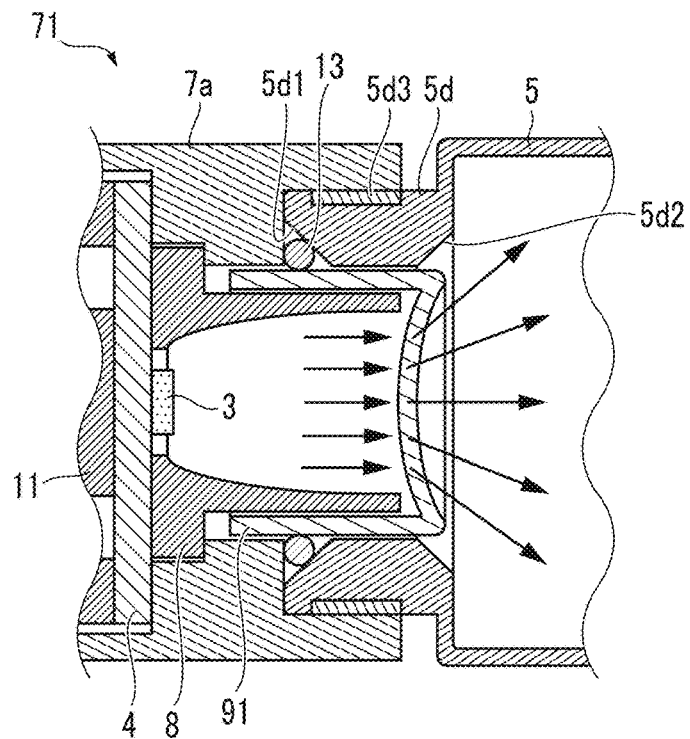
FIG. 3A is an enlarged view of the light source module device (a concave quartz cap)

FIG. 3A illustrates a light source module device 71 including the light source 3, the substrate 4, the reflector 8, the heat sink 11, and a quartz cap 91 all being held inside the frame 7a. The disposition of the respective members constituting the light source module device 71 is the same as that of the above-described light source module device 7 (refer to FIG. 2B) except that the top end portion of the quartz cap 91, through which the ultraviolet light passes, is formed concave relative to the open end surface of the reflector 8.

The ultraviolet light emitted from the light source 3 and reflected on the inner surface of the reflector 8 passes through the quartz cap 91 mounted so as to cover the reflector 8. The quartz cap 91 as well is made of quartz glass so as to have a substantially uniform thickness. The ultraviolet light is refracted when passing through the quartz cap 91 to be thereby diffused more largely than the ultraviolet light passing through the above-described quartz cap 9 (planar on its both sides). This enables efficient irradiation of the fluid in the channel with ultraviolet light.

Further, as the O-ring 13 is provided between the quartz cap 91 and the connection port 5d (the triangular groove 5d1) of the barrel body 5, invasion of the fluid into the light source module device 71 can be prevented. Being positioned so as to be rarely irradiated with the ultraviolet light, the O-ring 13 can be saved from deterioration.

Figure 3B:
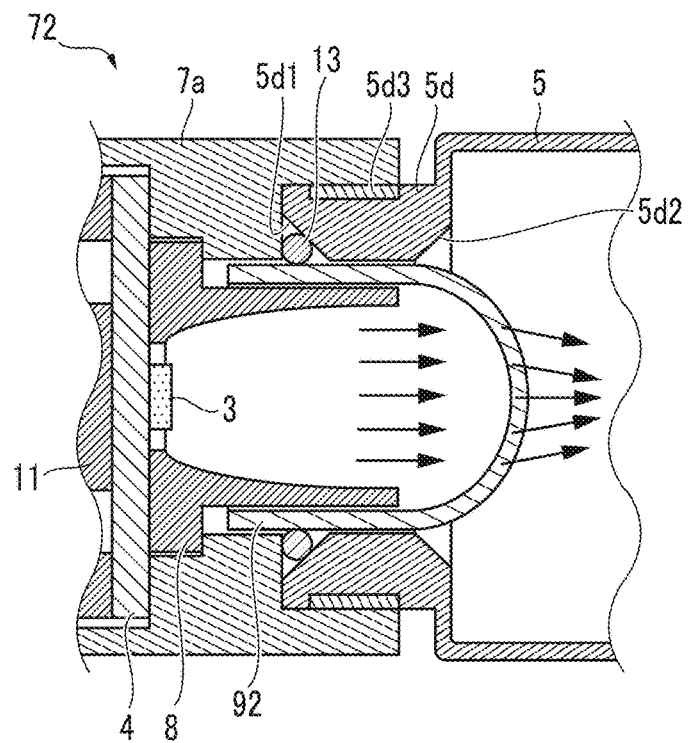
FIG. 3B is an enlarged view of the light source module device (a round quartz cap)

FIG. 3B illustrates a light source module device 72 including the light source 3, the substrate 4, the reflector 8, the heat sink 11, and a quartz cap 92 all being held inside the frame 7a. Here again, the disposition of the respective members constituting the light source module device 72 is the same as that of the above-described light source module device 7 (refer to FIG. 2B) except that the top end portion of the quartz cap 92, through which the ultraviolet light passes, is formed round (convex) relative to the open end surface of the reflector 8.

The ultraviolet light emitted from the light source 3 and reflected on the inner surface of the reflector 8 passes through the quartz cap 92 mounted so as to cover the reflector 8. The quartz cap 92 as well is made of quartz glass so as to have a substantially uniform thickness. The ultraviolet light is refracted when passing through the quartz cap 92 and thereby condensed, which is opposite from the case where the above-described quartz cap 9 (planar on its both sides) is used. Hence, this quartz cap 92 is most suitably used for intensive irradiation of a particular area on the fluid with ultraviolet light.

Further, as the O-ring 13 is provided between the quartz cap 92 and the connection port 5d (the triangular groove 5d1) of the barrel body 5, invasion of the fluid into the light source module device 72 can be prevented. Being positioned so as to be rarely irradiated with the ultraviolet light, the O-ring 13 can be saved from deterioration.

The quartz cap can have any other shapes. This allows selective use of a quartz cap in a suitable shape, depending on the purpose of use. The above-described quartz caps 9, 91, 92 have an additional advantage that the caps are readily exchangeable as being capped on the outer circumference of the reflector 8.

Figure 4A:
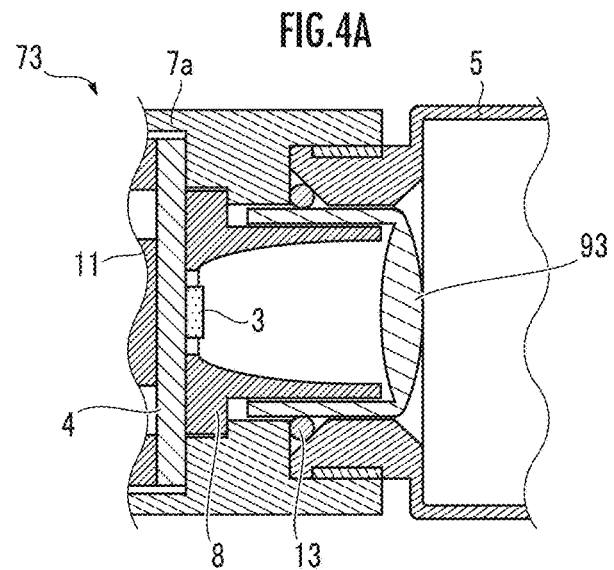
FIG. 4A is an enlarged view of the light source module device (a quartz cap that is convex on its both sides)

FIG. 4A illustrates a light source module device 73 having a quartz cap 93 that is shaped such that a portion thereof to be mounted on the reflector 8 has a substantially uniform thickness and a top end portion thereof, through which the ultraviolet light passes, is convex on its both sides. The quartz cap 93 can be used for light distribution control different from that with the above-described quartz caps 9, 91, 92.

Figure 4B:
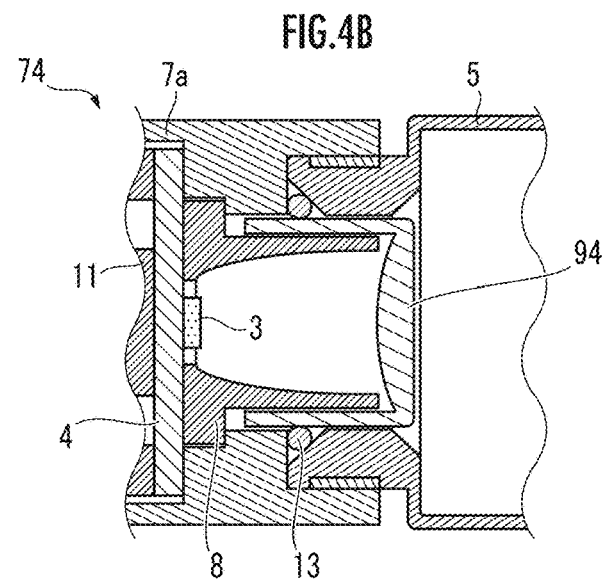
FIG. 4B is an enlarged view of the light source module device (a quartz cap that is convex on its one side)
Figure 4C:
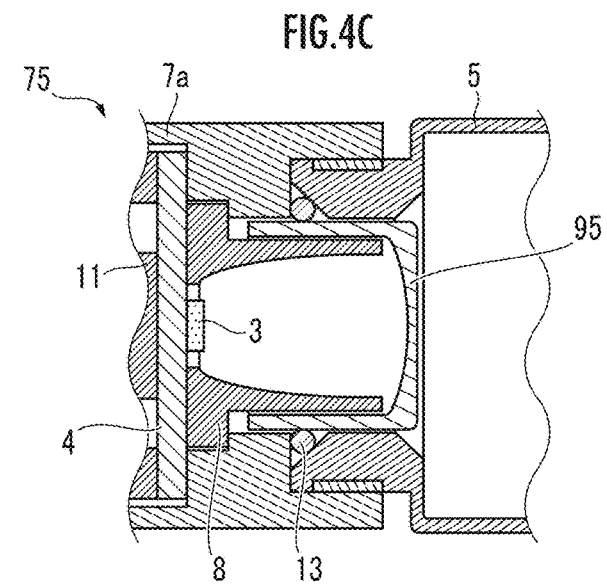
FIG. 4C is an enlarged view of the light source module device (a quartz cap that is concave on its both sides)

Alternatively, like the quartz cap 94 of the light source module device 74 illustrated in FIG. 4B, the top end portion of the quartz cap 94, through which the ultraviolet light passes, may be formed convex on its one side (on the side of the light source 3). Still alternatively, like the quartz cap 95 of the light source module device 75 illustrated in FIG. 4C, the top end portion of the quartz cap 95, through which the ultraviolet light passes, may be formed concave on its one side (on the side of the light source 3). Light distribution control for the respective quartz caps will be described later in detail.

In the following, referring to FIG. 5A to FIG. 5D, illumination distributions (results of simulation) of the ultraviolet light relative to the fluid flowing in the barrel body 5 will be described. Note that the illumination distributions described below are relevant to a case where fluid flows in the fluid sterilizing device 1 (refer to FIG. 1) under conditions that the light reflection rate of the reflector 8 is about 70% and the diffusion reflection rate of the inner surface of the barrel body 5 is about 20%.

Figure 5D:
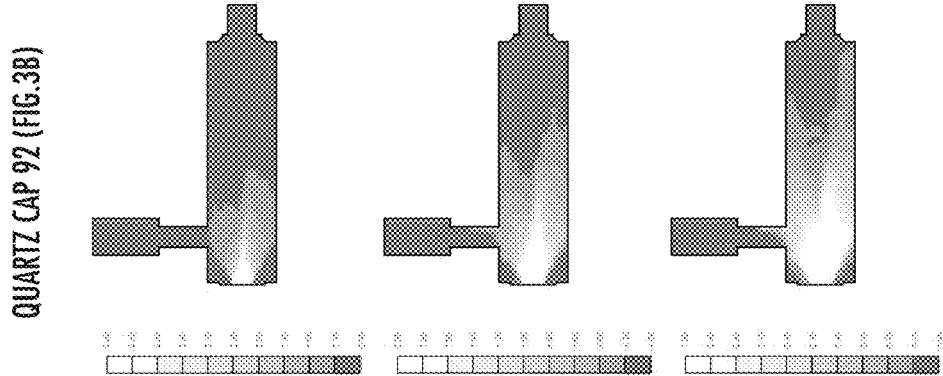
FIG. 5D illustrates illumination distributions with a quartz cap (round)
Figure 5C:
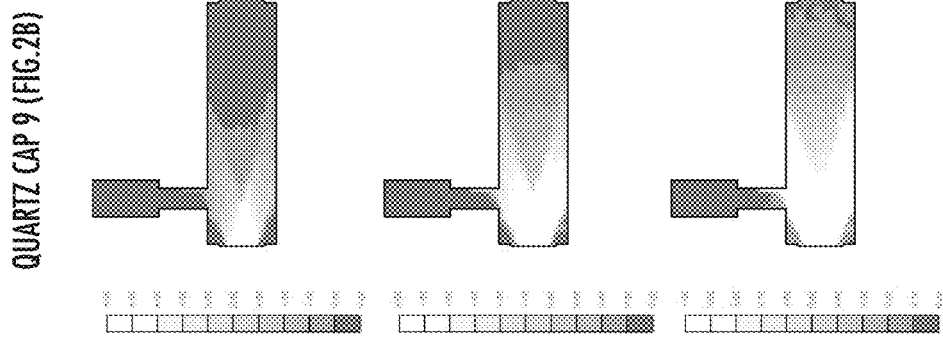
FIG. 5C illustrates illumination distributions with a quartz cap (planar on its both sides)
Figure 5B:
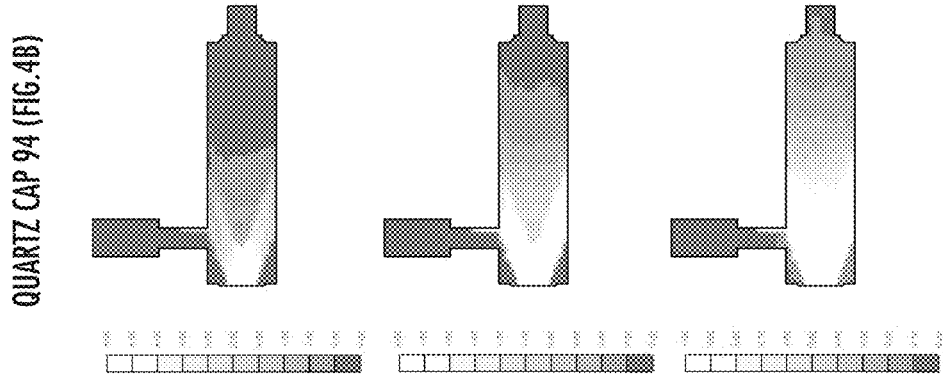
FIG. 5B illustrates illumination distributions with a quartz cap (convex on its one side)
Figure 5A:
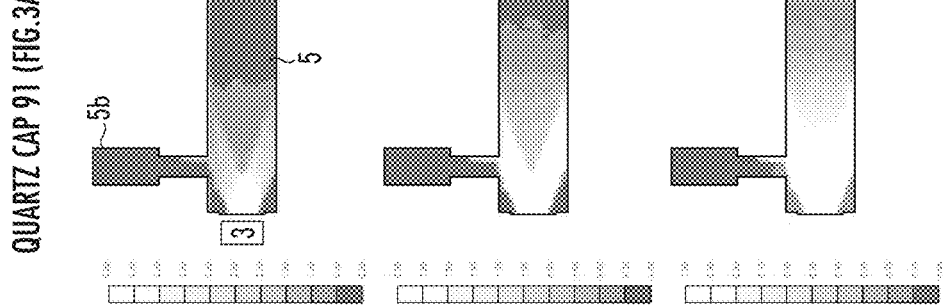
FIG. 5A illustrates illumination distributions with a quartz cap (concave)

In the upper section in FIG. 5A, an illumination distribution with the light source module device 71 illustrated in FIG. 3A (the concave quartz cap 91) employed is illustrated. It is known that, as the light source module device 71 including the light source 3 is disposed to the left of the barrel body 5, illumination is as strong as 5.0 (mW/cm$^2$) on the left end portion of the barrel body 5, and gradually drops in positions farther from the outlet 5b to become 0.5 (mW/cm$^2$) in positions farther from the middle of the barrel body 5 in the longitudinal axial direction.

In the middle section in FIG. 5A, an illumination distribution is illustrated with the scale in the range of 0 to 2 (mW/cm$^2$). In the lower section, an illumination distribution is illustrated with the scale in the range of 0 to 1 (mW/cm$^2$). According to the illumination distribution in the lower section, the quartz cap 91 can produce an illumination of about 0.20 (mW/cm$^2$) even on the right end portion of the barrel body 5.

In the upper section in FIG. 5B, an illumination distribution with the light source module device 74 illustrated in FIG. 4B (the quartz cap 94 that is convex on its one side) employed is illustrated. It is known from the illumination distribution that the quartz cap 94 can produce the same light distribution as that of the above-described quartz cap 91.

In the upper section in FIG. 5C, an illumination distribution with the light source module device 7 illustrated in FIG. 2B (the quartz cap 9 that is planar on its both sides) employed is illustrated. It is known from the illumination distribution in the lower section that the quartz cap 9 enables a wider diffusion angle of the ultraviolet light, compared with that with the above-described quartz cap 91.

Finally, in the upper section in FIG. 5D, an illumination distribution with the light source module device 72 illustrated in FIG. 3B (the round quartz cap 92) employed is illustrated. It is known from the illumination distribution that the quartz cap 92 can produce a condensed light distribution, which is opposite from that in the case where the above-described quartz cap 91 is used. In consideration of the above-described results of simulations, a quartz cap of a suitable kind can be properly selected to be used, depending on the purpose of use.

In the following, referring to FIG. 6 and FIG. 7, modifications of the light source module device will be described. Note that the structures same as those in the above-described embodiments are given the same reference numerals, and their descriptions are omitted.

Figure 6:
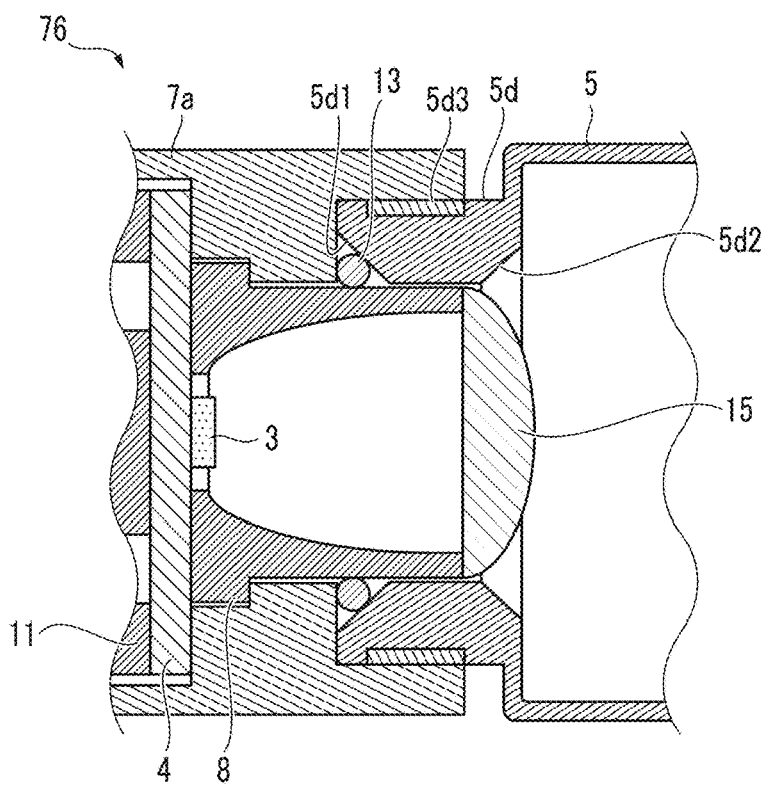
FIG. 6 is an enlarged view of a light source module device (a convex quartz lens)

FIG. 6 illustrates a light source module device 76 including the light source 3, the substrate 4, the reflector 8, the heat sink 11, and an optical lens 15, all being held inside the frame 7a. The disposition of the respective members constituting the light source module device 76 is basically the same as that of the above-described light source module device 7 (refer to FIG. 2B) except that the optical lens 15 is used instead of the quartz cap 9.

The optical lens 15 is a convex lens here, and welded to the open end surface of the reflector 8 for sealing. The sealing can prevent invasion of the fluid into the inside of the reflector 8. The O-ring 13 is disposed between the reflector 8 and the connection port 5d (the triangular groove 5d1) of the barrel body 5, which as well can block invasion of the fluid. Being positioned so as to be rarely irradiated with the ultraviolet light, the O-ring 13 can be saved from deterioration.

The ultraviolet light emitted from the light source 3 and reflected on the inner surface of the reflector 8 is refracted and thereby diffused when passing through the optical lens 15. This enables efficient irradiation of the fluid in the channel with ultraviolet light.

The optical lens 15 may be attached with Kovar alloy (Fe 54%, Ni 28%, Co 18%), whose coefficient of thermal expansion coincides with that of glass in a large range. This can reduce a stress to be applied due to a difference in coefficient of thermal expansion in attachment. Note that the optical lens may be a concave lens or a planar lens. As the respective lenses form different light distributions, a lens in a suitable kind can be selected to be used, depending on the purpose of use.

Although the reflector 8 as a single member is used in the above, similar light distribution control is achievable without the reflector 8. For example, the frame 7a is formed in a tapered structure so as to have a shape like that of a reflector. With the above, the same effect can be expected.

Figure 7:
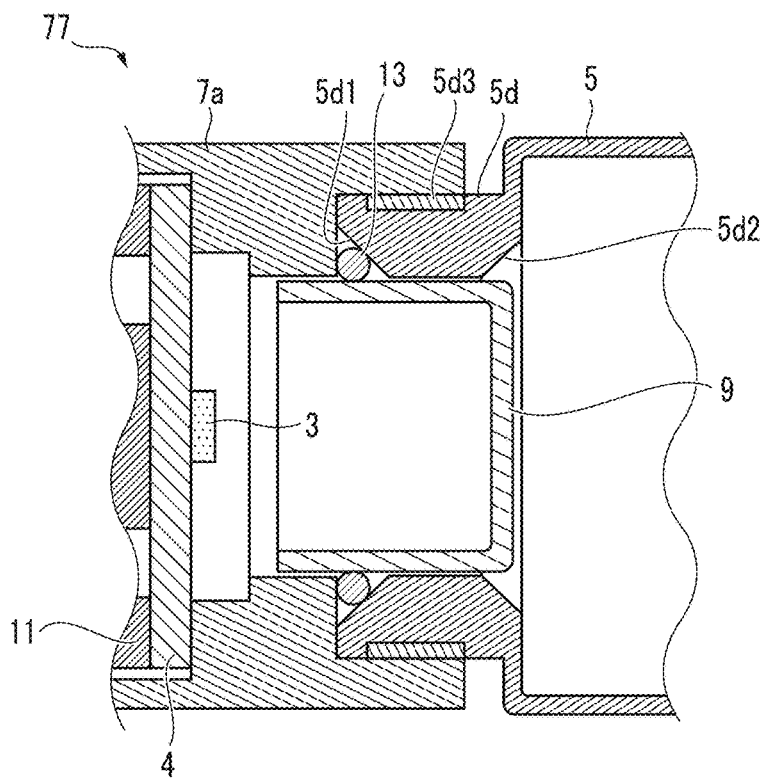
FIG. 7 is an enlarged view of a light source module device (a quartz cap that is planar on its both sides with no reflector)

FIG. 7 illustrates a light source module device 77 including the light source 3, the substrate 4, the quartz cap 9, and the heat sink 11 all being held in the frame 7a. The disposition of the respective members constituting the light source module device 77 is basically the same as that of the above-described light source module device 7 (refer to FIG. 2B) except that the reflector 8 is not included.

The quartz cap 9 is made of quartz glass so as to have a substantially uniform thickness, and formed so as to be planar relative to the open end surface of the frame 7a. As ultraviolet light is refracted and thereby diffused when passing through the quartz cap 9, it is possible to achieve efficient irradiation of the fluid in the channel with ultraviolet light. Here again, the top end portion of the quartz cap 9, through which the ultraviolet light passes, may be formed convex or concave relative to the open end surface of the frame 7a.

As illustrated, there is a gap between the quartz cap 9 and the connection port 5d of the barrel body 5, and the O-ring 13 is disposed in the gap. As a triangular groove 5d1 for the O-ring 13 is formed near the connection port 5d of the barrel body 5, invasion of the fluid into the light source module device 77 can be prevented.

The inner wall of the quartz cap 9 other than that of the top end portion of the quartz cap 9 may be covered with evaporated aluminum. With the above, as the ultraviolet light emitted from the light source 3 is reflected and led toward the fluid, the same effect as that of a reflector can be obtained.

Second Embodiment

Figure 8:
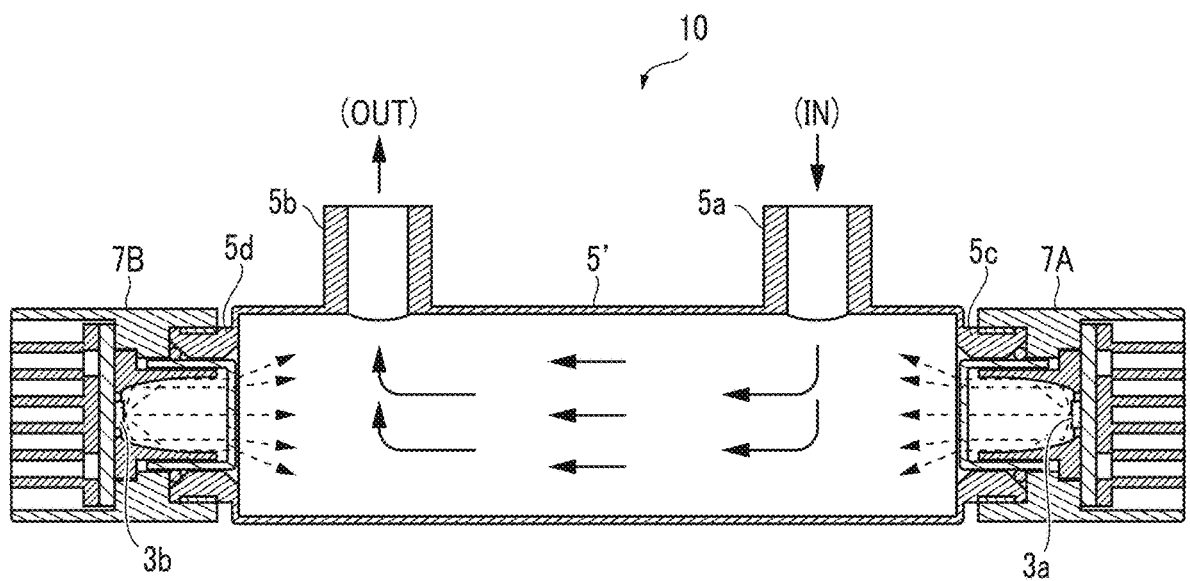
FIG. 8 is a cross sectional view of an entire fluid sterilizing device according to the present invention (a second embodiment)

A second embodiment of the fluid sterilizing device according to the present invention will be described referring to FIG. 8.

The fluid sterilizing device 10 has a channel, and includes a barrel body 5' constituting a sterilizing unit that sterilizes fluid and light source module devices 7A, 7B including LEDs, for example, as a light source.

In the second embodiment, an additional opening is formed on the barrel body 5 according to the first embodiment to make the additional opening as an inlet 5a. That is, fluid flows into the barrel body 5' through the inlet 5a (the inner diameter of 8.8 mm) formed on the outer circumference of the barrel body 5', and flows out through an outlet 5b (the inner diameter of 8.8 mm). In the above, the amount of fluid is 0.5 to 2 (L/min).

In addition, the light source module device 7A is mounted on the connection port 5c of the barrel body 5', and the light source module device 7B is mounted on the connection port 5d. Each of the light source module devices 7A, 7B includes a light source, a substrate, a reflector, a quartz cap, for example, all being held therein. Any of the above-described light source module devices 7, 71 to 77 can be used, depending on the purpose of use. Different light source module devices may be employed for the respective light source module devices 7A, 7B.

In the fluid sterilizing device 10, the fluid is irradiated with the ultraviolet light emitted from a light source 3a of the light source module device 7A immediately after flowing in through the inlet 5a, and with the ultraviolet light emitted from a light source 3b of the light source module device 7B in an area near the outlet 5b. This can improve efficiency in sterilization.

Third Embodiment

Figure 9:
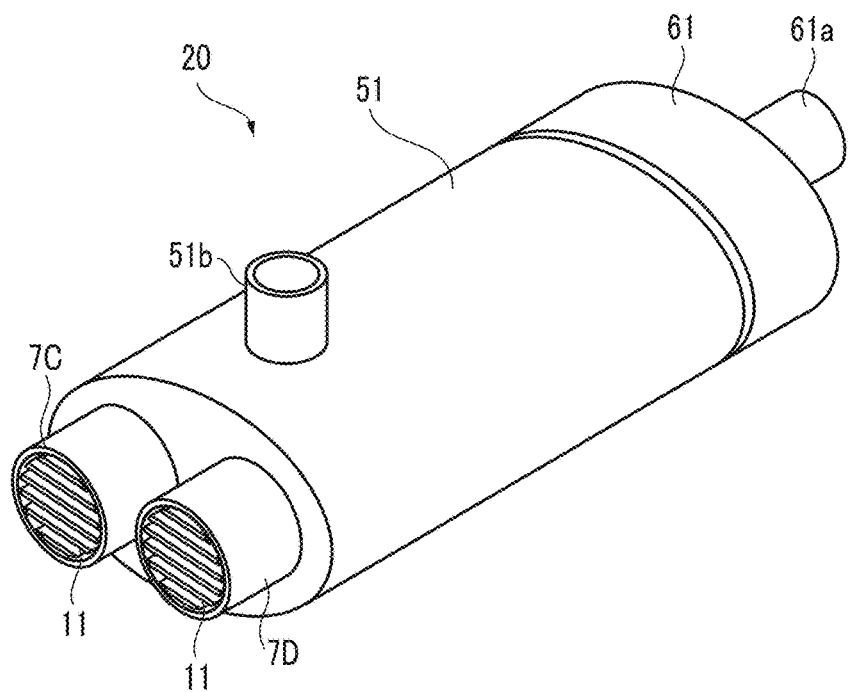
FIG. 9 is a cross sectional view of an entire fluid sterilizing device according to the present invention (a third embodiment).

Finally, a third embodiment of the fluid sterilizing device according to the present invention will be described referring to FIG. 9.

A fluid sterilizing device 20 has a channel, and includes a barrel body 51 constituting a sterilizing unit that sterilizes fluid and light source module devices 7C, 7D, including LEDs, for example, as a light source.

The barrel body 51 is made of stainless and shaped like a straight pipe whose cross section is oval and the length of which channel (sterilizing unit) is 100 mm Fluid, or a sterilizing target, flows in the longitudinal axial direction of the barrel body 51. The fluid flows into the barrel body 51 through an inlet 61a (the inner diameter of 13.4 mm) of an inflow device 61, the inlet 61a being formed on one end portion of the barrel body 51 in the axial direction, and flows out of the barrel body 51 through an outlet 51b (the inner diameter of 11.9 mm) formed on the outer circumference of the barrel body 51. In the above, the amount of fluid is larger, namely, 2 to 6 (L/min), than that of the above-described fluid sterilizing devices 1, 10.

On the other end portion in the axial direction (the end portion opposite from the inflow device 61) of the barrel body 51, light source module devices 7C, 7D are mounted. Each of the light source module devices 7C, 7D includes a light source, a substrate, a reflector, and a quartz cap, for example, all being held therein. Any of the light source module devices 7, 71 to 77 can be used, depending on the purpose of use. Different light source module devices may be employed for the respective light source module devices 7C, 7D, for example, such that one is of a condense type and the other is of a diffusion type. As described above, this device permits change in the number or kind of a light source module device to be mounted therein, depending on the amount of fluid in the barrel body 51, which can enhance efficiency in sterilization.

Note that the above-described embodiments are mere examples, and the member or material, for example, can be arbitrarily changed depending on use. As the amount of fluid flowing in the barrel body of the fluid sterilizing device differs depending on use, the dimension and shape of the barrel body are changeable. In particular, the light source module device according to the present invention is not limited to a flowing water reactor to be mounted on a part of a channel.

For example, the light source module device can be mounted on a server or a water tank having a dedicated connection port, so that the fluid in the vessel can be irradiated with ultraviolet light and thereby be sterilized. The fluid may be irradiated with ultraviolet light emitted from the side of the lateral surface of the vessel or the side of the upper surface of the vessel. This device can be utilized for surface sterilization or sterilization against water scales or mold in bathrooms.

The cross sectional shape of the barrel body can be of any polygon, not limited to a round or an oval. For example, three or more light source module devices may be mounted on an end portion of the enclosure, depending on the cross sectional area of the enclosure. In addition, the number of light sources in a single light source module device is arbitrarily changeable. For example, the light sources can be arranged in matrix depending on the shape of the cross section of the enclosure.

In an arrangement including a light source disposed on one side of the channel, like the fluid sterilizing device 1, the flowing direction of the fluid is generally opposite from the irradiation direction of the ultraviolet light. Alternatively, the flowing direction may be the same as the irradiation direction. The numbers and directions of inlets and outlets and the number of ultraviolet LEDs, for example, are arbitrarily changeable.

For a liquid sterilizing device whose inside wall of the barrel body is made of polyvinyl chloride, the inside wall may be coated with ultraviolet reflecting material or ultraviolet absorbing material to prevent deterioration of the polyvinyl chloride due to ultraviolet light. As ultraviolet reflecting material, aluminum or fluorine-based resin, such as polytetrafluoroethylene (PTFE) can be used. As ultraviolet absorbing material, stainless steel, for example, can be used.

REFERENCE SIGNS LIST 1, 10, 20 fluid sterilizing device, 3, 3a, 3b light source, 4 substrate, 5, 5', 51 barrel body 5a, 6a, 61a inlet, 5b, Mb outlet, 5c, 5d connection port, 6, 61 inflow device, 7, 7A to 7D, 7I to 77 light source module device, 7a frame, 8 reflector, 9, 91 to 95 quartz cap, 11 heat sink, 12 rectifier, 13 O-ring, 15 optical lens.

What is claimed is:

1. A fluid sterilizing device comprising:
a light source module device; and
an enclosure including a channel where fluid to be sterilized flows in an axial direction, at least one inlet through which the fluid to be sterilized flows in, and at least one outlet through which the fluid to be sterilized flows out, wherein
the light source module device includes:
a substrate;
a light emitting device mounted on the substrate configured to emit ultraviolet light;
a reflector disposed on the substrate so as to surround the light emitting element, and configured to reflect the ultraviolet light on an inner surface thereof to guide the ultraviolet light toward an irradiation target;
an optical device having a cap-like shape and mounted so as to cover an outer circumference of the reflector for transmitting, condensing, or diffusing the ultraviolet light; and
a frame disposed so as to surround an outer circumference of the cap-like shaped optical device, wherein
the at least one inlet is formed on one end portion of the enclosure in the axial direction,
the light source module device is attached to an end portion of the enclosure via a sealing structure, the end portion being opposite side of the at least one inlet,
a triangular groove is formed by the frame, the outer circumference of the cap-like shaped optical device, and the end portion of the enclosure at the opposite side of the at least one inlet, and
the sealing structure is disposed in the triangular groove, and seals between the cap-like shaped optical device and the end portion of the enclosure at the opposite side of the at least one inlet.

2. The fluid sterilizing device according to claim 1, wherein a portion of the optical device through which the ultraviolet light passes is formed convex, concave, or planar relative to an open end surface of the reflector.

3. A fluid sterilizing device comprising:
the light source module device according to claim 1; and
an enclosure including a channel where fluid to be sterilized flows in an axial direction, at least one inlet through which the fluid to be sterilized flows in, and at least one outlet through which the fluid to be sterilized flows out,
wherein
the at least one inlet and the at least one outlet are formed on an outer circumference of the enclosure, and
a second light source module device according to claim 1, wherein
the light source module device is attached to an end portion of the enclosure in the axial direction via a sealing structure as recited in claim 1,
the second light source module device is attached to another end portion of the enclosure in the axial direction via another sealing structure,
each of the two light source module devices includes a triangular grove formed by the frame, the outer circumference of the cap-like shaped optical device, and the respective end portion of the enclosure, and each sealing structure is disposed in the respective triangular grooves, and seals between the cap-like shaped optical device and the respective end portion of the enclosure.

4. A fluid sterilizing device comprising:

a light source module device; and an enclosure including a channel where fluid to be sterilized flows in an axial direction, at least one inlet through which the fluid to be sterilized flows in, and at least one outlet through which the fluid to be sterilized flows out, the light source module device includes:
- a substrate;
- a light emitting device mounted on the substrate configured to emit ultraviolet light;
- a reflector disposed on the substrate so as to surround the light emitting device, and which reflects the ultraviolet light on an inner surface thereof to guide the ultraviolet light toward an irradiation target; and
- an optical lens attached to an open end portion of the reflector to seal the reflector for condensing or diffusing the ultraviolet light, and
- a frame disposed so as to surround an outer circumference of the reflector wherein the at least one inlet is formed on one end portion of the enclosure in the axial direction, the light source module device is attached to an end portion of the enclosure via a sealing structure, the end portion being opposite side of the at least one inlet, a triangular groove is formed by the frame, the outer circumference of the reflector, and the end portion of the enclosure at the opposite side of the at least one inlet, and the sealing structure is disposed in the triangular groove, and seals between the reflector and the end portion of the enclosure at the opposite side of the at least one inlet.

* * * * *